United States Patent [19]

Ishihara et al.

[11] Patent Number: 4,792,387
[45] Date of Patent: Dec. 20, 1988

[54] AIR-FUEL RATIO DETECTING DEVICE

[75] Inventors: Toshiyuki Ishihara; Takeshi Kamiya; Yutaka Nakayama; Tetsusyo Yamada, all of Aichi, Japan

[73] Assignee: NGK Spark Plug Co., Ltd., Nagoya, Japan

[21] Appl. No.: 747,607

[22] Filed: Jun. 21, 1985

[30] Foreign Application Priority Data

Aug. 3, 1984 [JP] Japan ................................ 59-164098

[51] Int. Cl.⁴ ............................................ G01N 27/46
[52] U.S. Cl. .................................. 204/425; 204/412; 204/426
[58] Field of Search ................ 204/412, 425, 1 S; 338/34; 60/276; 123/489

[56] References Cited

U.S. PATENT DOCUMENTS

| | | | |
|---|---|---|---|
| 4,578,171 | 3/1986 | Yamada et al. | 204/412 |
| 4,578,172 | 3/1986 | Yamada et al. | 204/412 |
| 4,591,421 | 5/1986 | Yamada et al. | 204/426 |
| 4,594,139 | 6/1986 | Asayama et al. | 204/406 |
| 4,615,787 | 10/1986 | Yamada et al. | 204/425 |

Primary Examiner—T. Tung
Attorney, Agent, or Firm—Sughrue, Mion, Zinn, Macpeak, and Seas

[57] ABSTRACT

An air-fuel ratio detecting device with which the air-fuel ratio can be accurately detected over the entire range of ratios, both for the lean range and for the rich range. An oxygen pumping element and an oxygen sensing element are arranged opposite one another with a gap therebetween and are disposed in a chamber in which exhaust gas flows. A signal which is symmetric in lean and rich regions is thereby obtained, and this signal is divided into separate portions in the two regions, which are then composed to obtain a single-valued signal accurately representing the air-fuel ratio over the entire operating range.

5 Claims, 6 Drawing Sheets

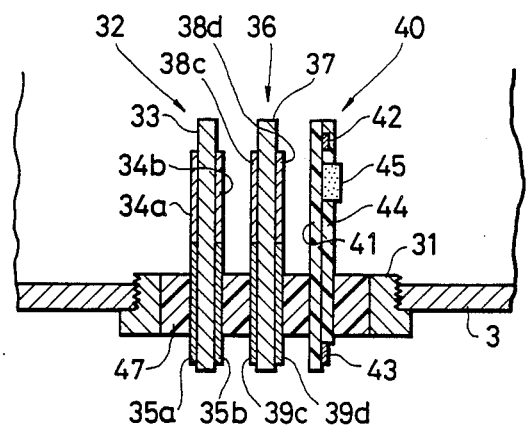
FIG. 3
FIG. 4
FIG. 5
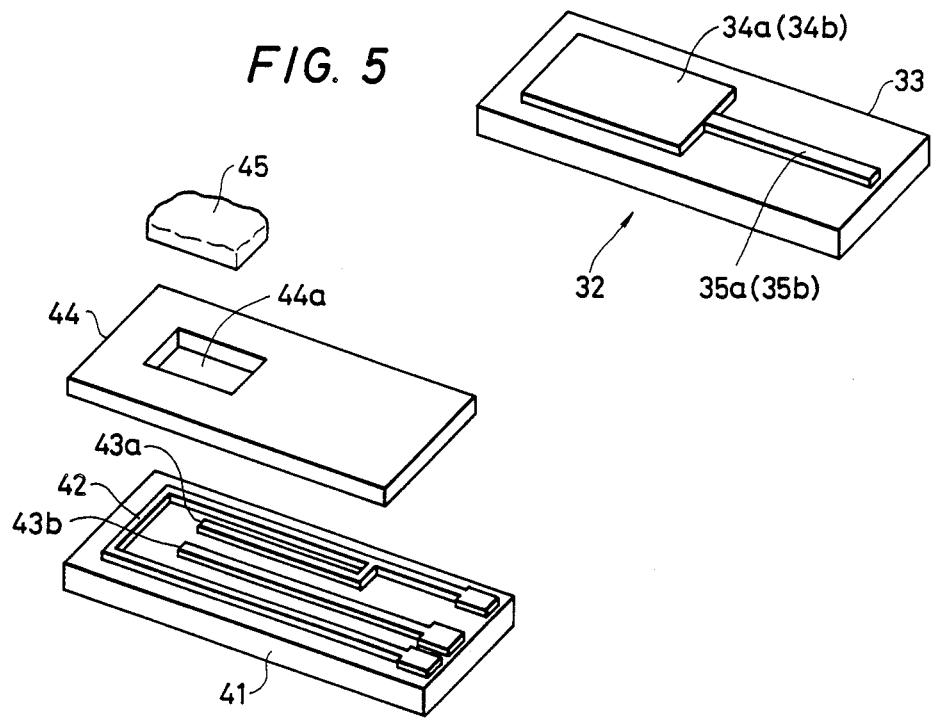

AIR-FUEL RATIO DETECTING DEVICE

BACKGROUND OF THE INVENTION

The present invention generally relates to an air-fuel ratio detecting for detecting the air-fuel ratio of an air-fuel mixture supplied to a combustion device, and particularly to an air-fuel ratio detecting device provided with a detecting element section in which an oxygen sensing element and an oxygen pumping element are disposed in opposition to each other with a gap therebetween, each of the two elements being made of an oxygen-ion-conductive solid electrolyte provided with porous electrodes on opposite surfaces thereof, whereby the air-fuel mixture can be accurately detected over the entire operating range from rich to lean.

Conventionally, in a combustion device such as an engine or the like, feedback control of the air-fuel mixture has been carried out by detecting the concentration of oxygen in the exhaust gas and controlling the intake air-fuel ratio so as to maintain it near a theoretical (stoichiometric) value, thereby to reduce the fuel consumption rate and maintain a low level of unwanted emissions. For the oxygen sensor used in the system, generally an oxygen sensor is employed of a type in which the output voltage changes in a switching mode at the theoretical air-fuel ratio. An example of such a sensor is an oxygen sensor in which an ion-conductive solid electrolyte is coated with a porous electrode layer, and the air-fuel ratio in the vicinity of the theoretical value is detected on the basis of variations in an electromotive force generated between the electrode layers due to a difference in oxygen partial pressure between the exhaust gas and the atmosphere.

Recently, it has been considered desirable that the air-fuel ratio of the air-fuel mixture not just be maintained at a value in the vicinity of the theoretical air-fuel ratio, but controlled to a desired value in accordance with the present running state of the engine so as to further improve fuel economy and reduce emissions as well as improve the overall running performance of the engine. In the conventional oxygen sensor described above, however, only the theoretical air fuel ratio of the air-fuel mixture could be unambiguously detected, and therefore it was impossible to control the air-fuel mixture to a desired air-fuel ratio.

In order to realize feedback control of the air-fuel ratio as described above, there has been proposed an oxygen sensor in which two elements, each made of a plate-like oxygen-ion-conductive solid electrolyte provided with electrode layers on its opposite surfaces, are mounted parallel to one another with a gap therebetween communicating with the exhaust gas. One of the elements is used as an oxygen pumping element and the other as an oxygen sensing element, the latter producing an output in accordance with the difference in oxygen density between the atmosphere and the gap. This sensor produces an accurate output in the lean region of the air-fuel mixture where there is residual oxygen in the exhaust gas. However, in the rich region where there is no residual oxygen, due to reaction with $CO$, $CO_2$, $H_2O$, and the like, the output of the sensor was not accurate.

SUMMARY OF THE INVENTION

Accordingly, an object of the present invention is to provide an air-fuel ratio detecting device which overcomes the drawbacks mentioned above.

In accordance with this and other objects, the invention provides an oxygen sensor having an oxygen pumping element and an oxygen sensing element arranged in opposition to one another and disposed with the gap therebetween in communication with a chamber in which exhaust gas flows, whereby a signal which is symmetric in a lean and a rich regions is obtained. This signal is divided into portions in the lean and rich regions, respectively, which are then composed to obtain a signal accurately and unambiguously representing the air-fuel ratio over the entire operating range from rich to lean, thereby making it possible to perform feedback control in such a manner that the air-fuel mixture can be controlled to any ratio.

More specifically, an air-fuel ratio detecting device according to the present invention comprises, as shown in the block diagram of FIG. 1:

a detecting element section I provided with first and second elements disposed in opposition to one another and disposed in a chamber in which an exhaust gas flows, each of the elements being made of an oxygen-ion-conductive solid electrolyte provided with porous electrodes on its opposite surfaces;

theoretical air-fuel ratio detecting means II for detecting a theoretical air-fuel ratio to produce a theoretical air-fuel ratio signal for determining whether the actual air-fuel ratio is in the lean region or in the rich region;

air-fuel ratio signal detecting means V employing the first and second elements of the detecting element section as an oxygen sensing element III and an oxygen pumping element IV, respectively, and an electromotive force of the oxygen sensing element III or a pumping current flowing in the oxygen pumping element IV are controlled so as to generate an air-fuel ratio signal corresponding to the air-fuel ratio in each of the lean and rich regions of air-fuel ratio; and actual air-fuel ratio signal detecting means VI receiving the theoretical air-fuel ratio signal produced by the theoretical air-fuel ratio detecting means and detecting an actual air-fuel ratio signal corresponding to an actual air-fuel ratio over the entire range of air-fuel ratios in such a manner that the air-fuel ratio signal produced by the air-fuel ratio signal detecting means is inverted when the actual air-fuel ratio is in a predetermined one of the lean and rich regions.

BACKGROUND OF THE INVENTION

FIG. 3 is a sectional view showing an oxygen sensor attached to an exhaust manifold;

FIG. 4 is an explanatory diagram used for explaining the structure of an oxygen sensing element;

FIG. 5 is an explanatory diagram used for explaining the structure of a theoretical air-fuel ratio detecting element;

DESCRIPTION OF THE PREFERRED EMBODIMENTS

Figure 1:
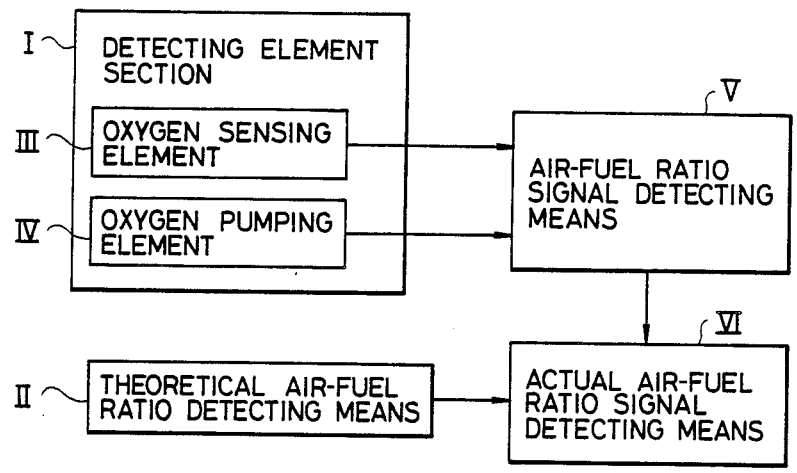
FIG. 1 is a block diagram showing the overall arrangement of an air-fuel ratio detecting device according to the present invention.

Referring to the drawings, a preferred embodiment of an air-fuel ratio detecting device constructed according to the present invention will be described hereunder.

Figure 2:
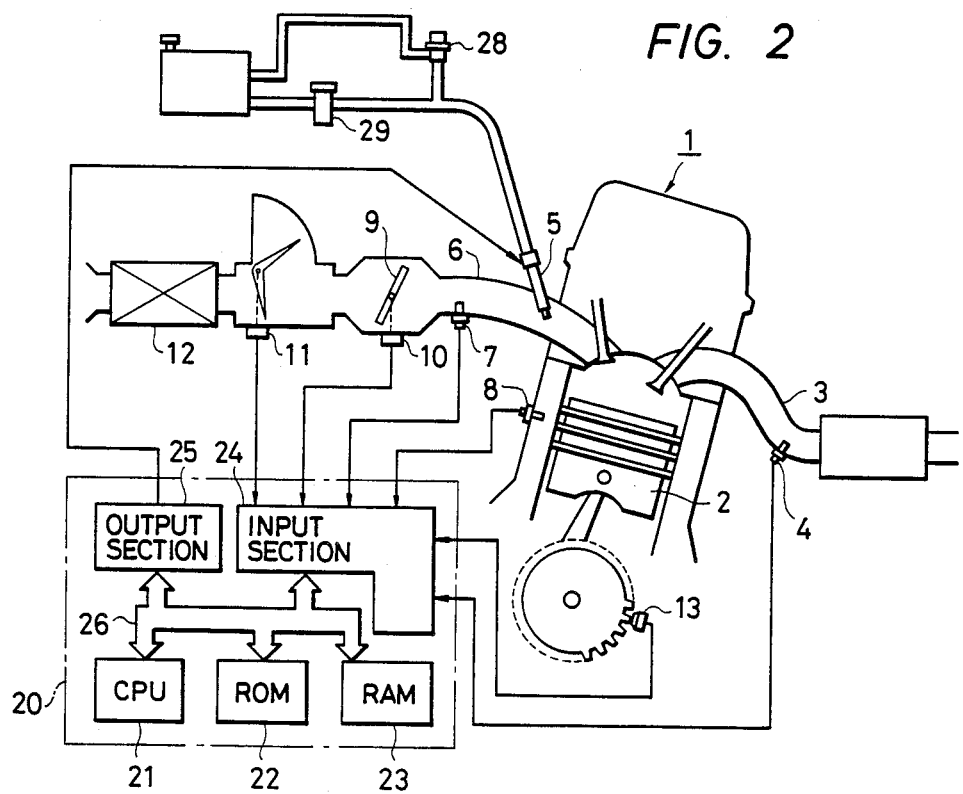
FIG. 2 is a schematic system diagram showing an engine on which the air-fuel ratio detecting device of the invention is mounted.

FIG. 2 is a schematic system diagram showing an internal combustion engine system employing an air-fuel ratio detecting device of the invention. In this drawing, reference numeral 1 designates an engine; 2, a piston; 3, an exhaust manifold; 4, an oxygen sensor provided at the exhaust gas manifold for detecting the air-fuel ratio of the air-fuel mixture supplied to the engine 1; 5, fuel injection valves provided at each cylinder for injecting fuel; 6, an intake manifold; 7, an intake-air temperature sensor mounted on the intake manifold 6 for detecting the temperature of the intake air; 8, a coolant-temperature sensor for detecting the temperature of the coolant for the engine 1; 9, a throttle valve; 10, a throttle opening sensor for detecting the degree of opening of the throttle valve 9; 11, a flowmeter for detecting the flow rate of the intake air; 12, an air cleaner for cleaning the intake air; and 13, an engine speed sensor producing a signal indicative of the rotational speed of the engine 1.

Further, reference numeral 20 designates an electronic control circuit composed of a microcomputer and having a central processing unit (CPU) 21 receiving and operating upon data produced by the sensors described above on the basis of a control program and driving the fuel injection valves 5 to control the quantity of fuel injected in accordance with the running state of the engine 1; a read-only memory (ROM) 22 in which data such as the control program and the like are stored in advance; a random-access memory (RAM) 23 in which data required for various operating procedures such as data received from the sensors and the like are temporarily stored; an input section 24 provided with a waveform shaper circuit responsive to the respective signals from the sensors, an A/C converter, and a multiplexer for selectively applying a waveform-shaped digital signal to the CPU 21; an output section 25 for producing a drive signal for the fuel injection valves 5 in accordance with the quantity of injected fuel calculated by the CPU 21; and a bus 26 connecting the respective elements such as the CPU 21, the ROM 22, the RAM 23, and input and output sections 24 and 25. The drive signal produced by the electronic control circuit 21 as described above is applied to the fuel injection valves 5, and fuel having a pressure adjusted by a fuel adjusting valve 28 and supplied by a fuel pump 29 is accordingly injected.

Next, a description will be given of the oxygen sensor 4, which is an important aspect of the present invention. The oxygen sensor 4 in this embodiment is provided not only with an oxygen sensing element (III) and an oxygen pumping element (IV) as described above, but also with a theoretical air-fuel ratio detecting element (corresponding to the theoretical air-fuel ratio detecting means II) in which a metal oxide semiconductor layer is formed on the surface of an electrically insulating member.

FIG. 3 is a sectional view showing the oxygen sensor 4 mounted on the exhaust manifold 3. In this drawing, the oxygen sensor 4 is attached via an oxygen-sensor hole formed in the exhaust manifold 3 through an attachment member 31. Reference numeral 32 designates an oxygen sensing element arranged such that, as shown in FIG. 4, porous platinum electrode layers 34a and 34b, each having a thickness of about 20 microns, and platinum electrodes 35a and 35b, used for deriving an output, are formed on opposite side surfaces of a planar, ion-conductive solid electrolyte 33 having a thickness of about 0.5 mm and formed using a thick-film technique. The ion-conductive solid electrolyte 33 is made of, for example, stabilized or partially stabilized zirconia, thoria, ceria, or the like. Reference numeral 36 designates an oxygen pumping element wherein porous platinum electrode layers 38c and 38d, and platinum electrodes 39c and 39d are formed on the opposite side surfaces of an ion-conductive solid electrolyte 37 in the same manner as the oxygen sensing element 32 described above.

Reference numeral 40 designates the theoretical air-fuel ratio detecting element wherein, as shown in FIG. 5, a heating resistive pattern 42 and electrode patterns 43a and 43b are formed on a side surface of a planar, electrically insulating member 41 made of, for example, alumina or the like and having a thickness of 0.7 mm, also formed by a thick-film technique. An electrically insulating member 44 having a thickness of 0.1 mm is integrally sintered on the surfaces of the foregoing patterns, the electrically insulating member 44 being formed with an opening portion 44a through which the electrodes 43a and 43b are exposed. A metal oxide segment 45 having a thickness of about 150 microns is provided in the opening portion 44a abutting the electrode patterns 43a and 43b, the metal oxide segment 45 being made of, for example, titania or the like.

The oxygen sensing element 32, the oxygen pumping element 36, and the theoretical air-fuel ratio detecting element 40 are arranged in opposition to each other through a heat-resistant, electrically insulating spacer 47 with a small gap about 0.1 mm wide between the oxygen sensing element 32 and the oxygen pumping element 36 and a small gap of about 0.1 mm between the oxygen pumping element 36 and the theoretical air-fuel ratio detecting element 40. The spacer 47 is attached to the exhaust manifold 3 through the attachment member 31. For the material of the spacer 47, heat-resistant, electrically-insulating filler adhesives may be used. According to the present invention, the gap between the oxygen sensing element 32 and the oxygen pumping element 36 forms a diffusion chamber. The gap is not limited to the case where it is opens widely at its edge, and it may be almost closed at its edge with only a small hole communicating with the exhaust gas.

Next, a description will be given of the air-fuel ratio signal detecting circuit (corresponding to the air-fuel ratio signal detecting means V) in which a pumping current flowing in the oxygen pumping element 36 is controlled in such a manner as to maintain the output voltage of the oxygen sensing element 32 at a predetermined value, and a signal corresponding to the air-fuel ratio is derived accordingly.

Figure 6:
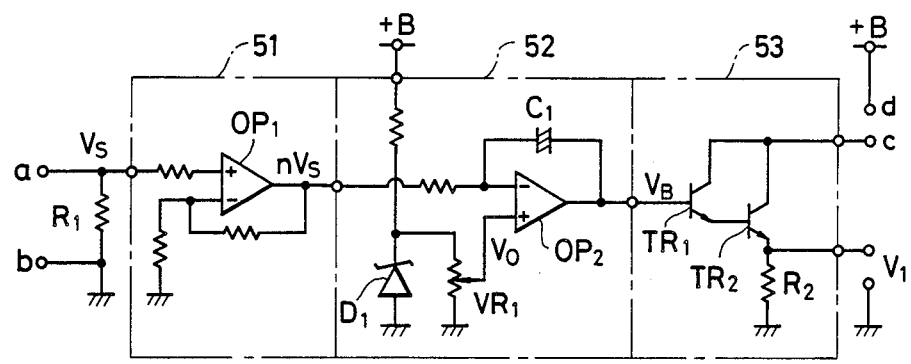
FIG. 6 is a circuit diagram showing an air-fuel ratio signal detecting circuit.
Figure 7:
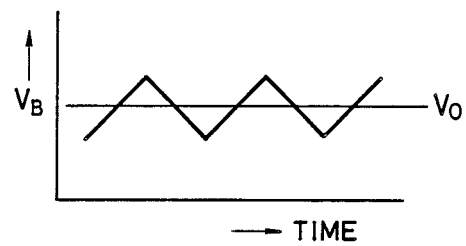
FIG. 7 is a voltage waveform diagram showing a control voltage $V_B$ produced by an integrator circuit and used for controlling a pumping current.

FIG. 6 is a circuit diagram showing the detecting circuit. In this drawing, terminals a, b, c and d are connected to the platinum electrodes 35a and 35b of the oxygen sensing element 32 and the platinum electrodes 39c and 39d of the oxygen pumping element 36, respectively. A voltage $V_s$ produced by the oxygen sensing element 32 corresponding to the density of oxygen or the density of $CO$, $CO_2$, $H_2O$, or the like in the exhaust gas is detected across a resistor R1 and amplified by an amplifier section 51, mainly composed of an operational amplifier OP1, to obtain a voltage $nV_s$, that is, a signal n times (for example, five times) as large in amplitude as the voltage $V_s$. The voltage $nV_s$ is applied to an integrator circuit 52, mainly composed of an operational amplifier OP2, and there is integrated using a reference voltage $V_0$ as a reference. As shown in FIG. 7, the reference voltage $V_0$ is obtained from a fixed voltage of a zener diode D1 divided by a variable resistor VR1. The integrated voltage is applied as a base voltage $V_B$ of a transistor TR1 in a pumping current controlling circuit 53 constituted by transistors TR1 and TR2. The output of this circuit controls the pumping current. In the drawing, +B designates a battery voltage.

Figure 8:
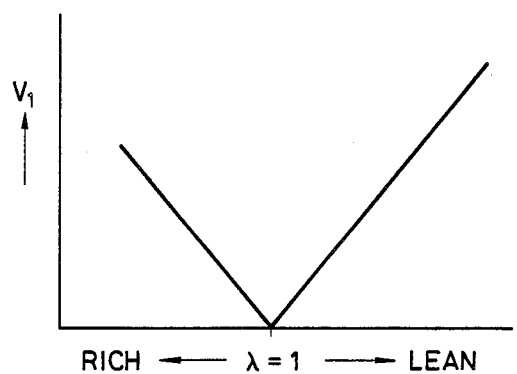
FIG. 8 is a diagram showing an air-fuel ratio signal $V_2$ detected by the air-fuel ratio detecting circuit.

Thus, the pumping current flowing in the oxygen pumping element 36 is controlled so that the concentration of oxygen in the gap between the oxygen sensing element 32 and the oxygen pumping element 36 is controlled, and hence the oxygen sensing element 36 outputs a predetermined voltage. Therefore, the pumping current of the oxygen pumping element 36 can be taken as an air-fuel ratio signal $V_1$ derived across a resistor R2. The air-fuel ratio signal $V_1$ in the lean and rich ranges of the air-fuel mixture is graphed in FIG. 8. In FIG. 8, $\lambda = 1$ designates the theoretical air-fuel ratio.

Figure 9:
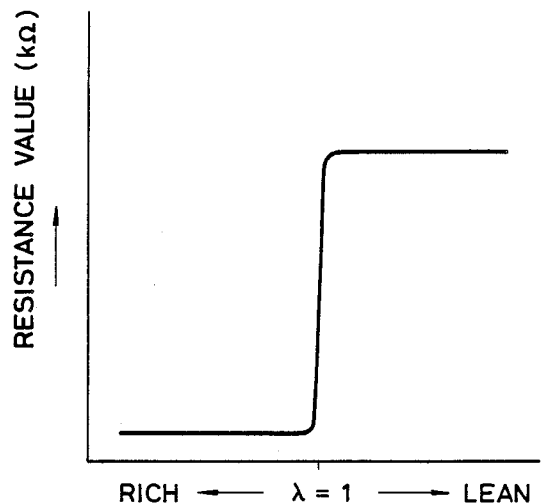
FIG. 9 is a diagram showing variations in resistance values of a metal oxide semiconductor body.

Further, as shown in FIG. 9, the resistance of the metal oxide semiconductor segment 45, made of titania or the like, of the theoretical air-fuel ratio detecting element 40 changes radially at the theoretical value; that is, it is large in the lean region and small in the rich region. This performance is due to the fact that the density of oxygen in the exhaust gas becomes zero at the theoretical value.

Further as is apparent from FIG. 5, one electrode pattern 43a of the electrode patterns 43a and 43b joined to the metal oxide semiconductor segment 45 is connected to the heating resistive pattern 42.

Figure 10:
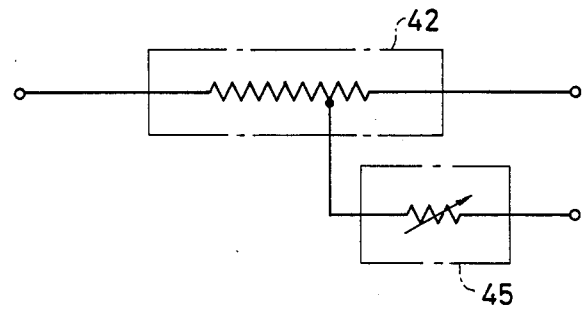
FIG. 10 is a circuit diagram showing a theoretical air-fuel ratio detecting element.

FIG. 10 is an electric circuit diagram of the theoretical air-fuel ratio detecting element 90. The signal which is detected by the theoretical air-fuel ratio detecting element 40 and which represents whether the air-fuel ratio of the air-fuel mixture is in the rich region or lean region with respect to the theoretical air fuel ratio, that is, the signal which represents the magnitude of the resistance value of the metal oxide semiconductor segment 45, can be detected by dividing a voltage supplied to the heating resistive pattern 42 to provide a predetermined voltage, for example, 1 volt, which is applied to the metal oxide semiconductor segment 45 and the current flowing through the segment 45 measured.

Figure 11:
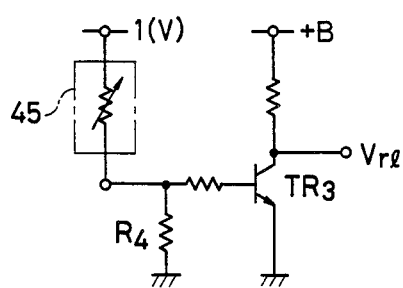
FIG. 11 is a circuit diagram showing a theoretical air-fuel ratio detecting circuit.

The detecting circuit for detecting the theoretical air-fuel ratio signal may be arranged, for example, as shown in FIG. 11, such that the current flowing in the metal oxide semiconductor segment 45 is detected as a voltage signal by the use of a resistor R4, which voltage controls the ON-OFF state of a transistor TR3. That is, when the air-fuel ratio is in the rich region, the resistance value of the metal oxide semiconductor segment 45 is small so that the voltage applied to the resistor R4 becomes large, making the transistor TR3 ON, which causes the collector voltage of the transistor TR3 to be zero. On the other hand, when the air-fuel ratio is in the lean region, the resistance value of the metal oxide semiconductor segment 45 is large and the voltage applied to the resistor R4 is very small, thereby making the transistor TR3 OFF, whereupon the collector thereof is at the battery voltage. Therefore, an H-level (high) signal is present when the air-fuel ratio is in the lean region, while an L-level (low) signal is present when the air-fuel ratio is in the rich region. Hereinafter, this signal is referred to as a theoretical air-fuel ratio signal $V_{rl}$.

The air-fuel ratio signal detecting circuit of FIG. 6 and the theoretical air-fuel ratio signal detecting circuit of FIG. 11, as described above, are provided in the input section 25 of the electronic control circuit 20. To detect the air-fuel ratio of the air-fuel mixture supplied to the engine 1, the respective detected signals are applied to the input section 25 through processing carried out by the CPU 21.

Figure 12:
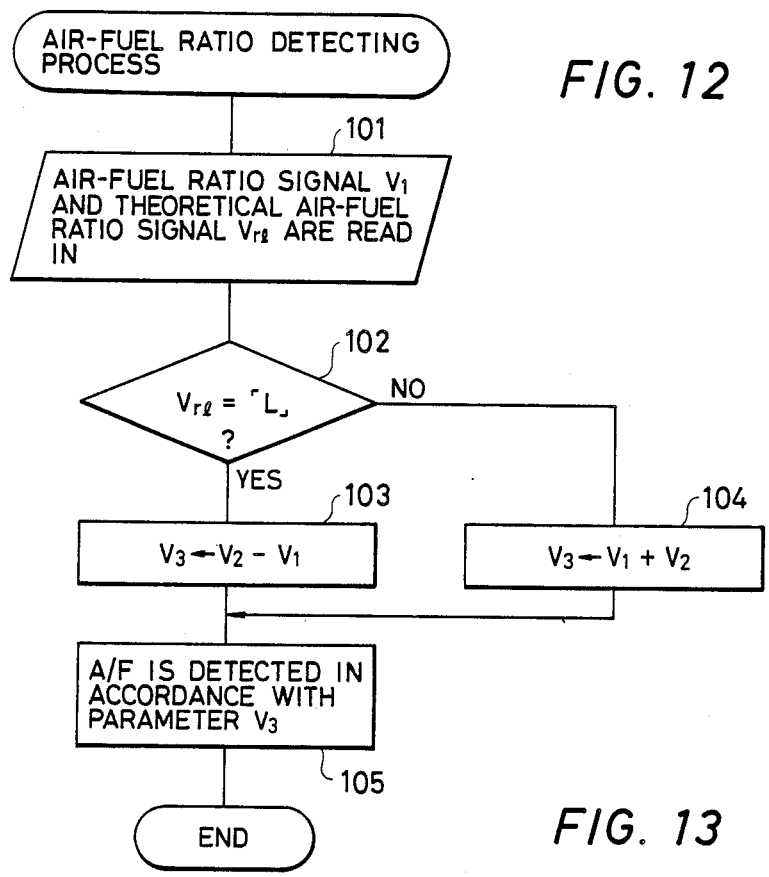
FIG. 12 is a flowchart showing air-fuel ratio detecting processing.

Referring to the flowchart of FIG. 12 showing a control program, a description will be given as to the air-fuel ratio detection processing. The air-fuel ratio detection processing is executed as a main routine in which the quantity of fuel injected is calculated to perform drive control for the fuel injection valves 5 such that the running state of the engine 1 is controlled on the basis of the respective output signals from the various sensors so as to satisfy certain feedback control conditions.

Upon initiation of the processing, step 101 is first executed such that the air-fuel ratio signal $V_1$ and the theoretical air-fuel ratio signal $V_{rl}$, respectively produced by the air-fuel ratio signal detecting circuit and the theoretical air-fuel ratio signal detecting circuit, are read in. In the next step 102, a judgment is made as to whether the read-in theoretical air-fuel ratio signal $V_{rl}$ is at the H level or not, that is, whether the air-fuel ratio of the air-fuel mixture is in the rich region or not. If the result is that the signal $V_{rl}$ is at the L level, the operation is shifted to step 103 in which the air-fuel ratio signal $V_1$, read in in the previous step 101, is subtracted from a set voltage $V_2$, thereby calculating an actual air-fuel ratio signal $V_3$ ($=V_2-V_1$). On the other hand, if the result is that the signal $V_{rl}$ is at the H level, the operation is shifted to step 104 in which the air-fuel ratio signal $V_1$, read in in the step 101, and the set voltage $V_2$ are added to calculate the actual air-fuel ratio signal $V_3$ ($=V_1+V_2$). After the actual air-fuel ratio signal $V_3$ has been obtained in step 103 or step 104, the operation is shifted to the next step 105 in which the air-fuel ratio of the intake mixture is obtained by using a map or predetermined algorithm in accordance with the value of the actual air-fuel ratio signal $V_3$. At this point, the air-fuel ratio detecting processing is completed.

Figure 13:
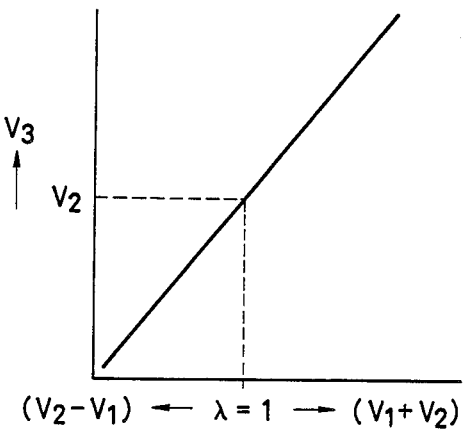
FIG. 13 is a diagram showing an actual air-fuel ratio signal $V_3$.

The air-fuel ratio detecting processing described above may be performed by adding the air-fuel ratio signal $V_1$ to or subtracting it from the set voltage $V_2$, as determined by the state of the theoretical air-fuel ratio signal $V_{rl}$, to obtain an actual air fuel ratio signal $V_3$ from which the air-fuel ratio can be determined. That is, as shown in FIG. 13, the air-fuel ratio signal $V_1$ of FIG. 8 obtained from the air-fuel ratio signal detecting circuit shown in FIG. 6 is inverted at the point corresponding to the theoretical air-fuel ratio ($\lambda = 1$) and corrected using the set voltage $V_2$ such that the value does not become negative. Therefore, the actual air-fuel ratio signal $V_3$ obtained in step 103 or 104 has a value unambiguously corresponding to the actual air-fuel ratio, and thus the actual air-fuel ratio can be obtained using the actual air-fuel ratio signal $V_3$ as a parameter.

According to the air-fuel detecting device of this embodiment, the air-fuel ratio of the intake mixture can be accurately detected over the entire operating range, and therefore the running state of the engine 1 can be accurately controlled to improve the fuel economy, reduce emissions, etc., and the air-fuel mixture can be controlled to have a desired air-fuel ratio so as to make it possible to perform more precise feedback control.

Although the heater portion for activating the elements of the oxygen sensor 4 is provided in the theoretical air-fuel ratio detecting element 40 in this embodiment, it may be provided, for example, in the oxygen sensing element 32 or in the oxygen pumping element 36. Moreover, although the theoretical air-fuel ratio detecting device 40 is integrated with the oxygen sensing element 32 and the oxygen pumping element 36 in the oxygen sensor 4, it is sufficient to arrange the oxygen sensing element 32 and the oxygen pumping element 36 in opposition to each other through a gap, and the theoretical air-fuel ratio detecting element 40 may be provided at another part of the exhaust manifold 3. Further, any theoretical air-fuel ratio detecting device is sufficient so long as it can detect whether the actual air-fuel ratio is in the rich or lean region. For example, a battery-type device using a solid electrolyte may be used instead of the theoretical air-fuel ratio detecting element 40 described above. Alternatively, detection may be performed on the basis of the resistance of the oxygen sensing element 32 or the oxygen pumping element 36.

Figure 14:
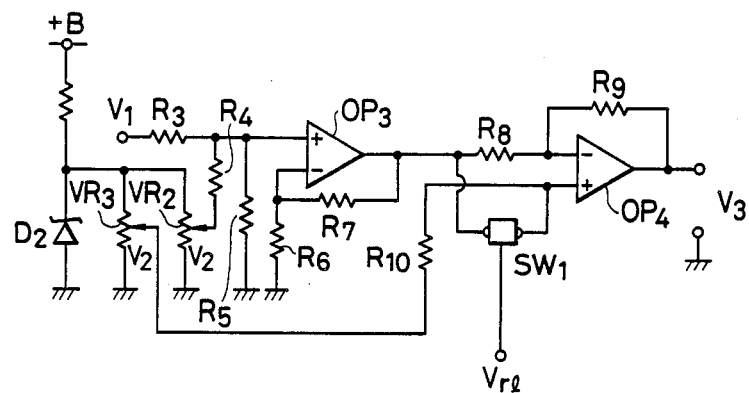
FIG. 14 is a circuit diagram showing an actual air-fuel ratio signal detecting circuit arranged to detect an actual air-fuel ratio signal $V_3$.

Although the actual air-fuel ratio detecting element is described in the foregoing by way of the example of air-fuel ratio detecting processing performed in the electric control circuit 20, the actual air-fuel ratio signal $V_3$ may be obtained using an actual air-fuel ratio signal detecting circuit as shown in FIG. 14, that is, without using a microcomputer.

As shown in FIG. 14, the air-fuel ratio signal $V_1$ produced by the air-fuel ratio signal detecting circuit shown in FIG. 6 is applied to the noninverting input terminal of an operational amplifier OP3 through a resistor R3, and a set voltage $V_2$ obtained by dividing a predetermined voltage determined by a zener diode $D_2$ by a variable resistor VR2 is applied through a resistor R4. Further, the noninverting input terminal of the operational amplifier OP3 is grounded through a resistor R5. On the other hand, the inverting input terminal of the operational amplifier OP3 is grounded through a resistor R6 and connected to the output terminal thereof through a resistor R7. The relationship among the resistances of the resistors R3 through R7 is as follows:

$$R3 = R4 = 2 \cdot R5 = R6 = R7/3$$

Therefore, a voltage $V_1 + V_2$ obtained by adding the air-fuel ratio signal $V_1$ to the set voltage $V_2$ is produced at the output terminal of the operational amplifier OP3.

The voltage $V_1 + V_2$ is applied to the inverting input terminal of an operational amplifier OP4 through a resistor R8, and further the inverting input terminal is connected to the output terminal of the amplifier OP4 through a resistor R9. A set voltage $V_2$ as determined by the zener diode $D_2$ and a variable resistor VR3 is applied to the noninverting input terminal of the operational amplifier OP4 through a resistor R10. An analog ON/OFF switch SW1 is turned ON/OFF in response to the theoretical air-fuel ratio signal $V_{rl}$ produced by the theoretical air-fuel ratio detecting circuit described above. The switch SW1 is in its ON state so as to connect the noninverting input terminal of the operational amplifier OP4 to the output terminal of the operational amplifier OP3 when the signal $V_{rl}$ is at the H level, that is, when the air-fuel ratio is in the lean region, while it is OFF so as not to connect the noninverting input terminal of the operational amplifier OP4 to the output terminal of the operational amplifier OP3 when the signal $V_{rl}$ is at the L level, that is, when the air-fuel ratio is in the rich region. Further, the resistors R8 to R10 have the same resistance values, and therefore the circuit operates only as a buffer circuit in the case where the air-fuel ratio is in the lean region, whereupon an unamplified voltage having a value of $V_1 + V_2$ is produced at the output terminal of the operational amplifier OP4, while, in the case where the air-fuel ratio is in the rich region, a voltage having a value of $V_2 - V_1$ is produced.

In the manner described above, with signals produced by the air-fuel ratio signal detecting circuit processed as described above, the output voltage has a value of $V_1 + V_2$ when the air-fuel ratio is in the lean region, and thus an actual air-fuel ratio signal $V_3$ corresponding to the actual air-fuel ratio is obtained, as shown in FIG. 13.

Although the above-described embodiment is arranged such that the air-fuel ratio signal $V_1$ is inverted in the rich region by using the theoretical air-fuel ratio ($\lambda = 1$) as a reference value so that the actual air-fuel ratio signal $V_3$ increases from the rich region to the lean region, the circuit may be modified such that the air-fuel ratio signal $V_1$ is inverted in the lean region so that the actual air-fuel ratio signal $V_3$ becomes smaller from the rich region to the lean region. Alternatively, if necessary, the device may be used only as a rich or lean region sensor by cutting off the air-fuel signal $V_1$ in the lean or rich region, respectively.

Figure 15:
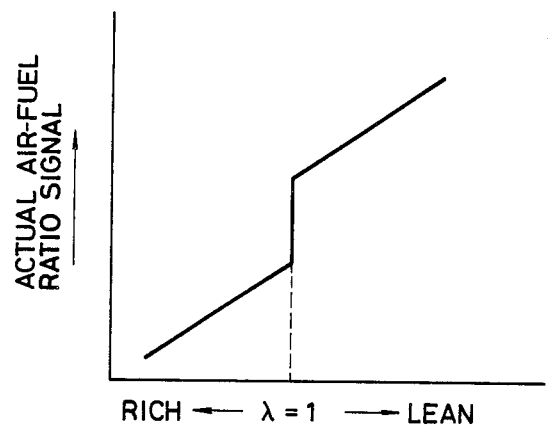
FIG. 15 is a diagram showing an actual air-fuel ratio signal which changes stepwise at a point corresponding to the theoretical air-fuel ratio.

Although the foregoing embodiment is arranged such that the actual air-fuel ratio signal $V_3$ continuously changes from the rich to the lean region of air-fuel ratio, for example, the respective voltages established by the variable resistors VR2 and VR3 shown in FIG. 14 can be made to have values different from each other so that the actual air-fuel ratio signal changes in a stepwise manner as shown in FIG. 15 at the point where the actual air-fuel ratio is the theoretical value, that is, where the excess air factor becomes equal to one ($\lambda = 1$). In such an arrangement where the actual air-fuel ratio signal which changes stepwise at the point $\lambda = 1$, a determination can be accurately made as to whether the actual air-fuel ratio is in the rich or lean region with respect to the theoretical air-fuel ratio, even if a detection delay occurs in the air-fuel ratio signal. In this case, it is made possible to more accurately control the air-fuel ratio in the vicinity of the theoretical air-fuel ratio.

As described above in detail, the air-fuel ratio detecting device according to the present invention is provided with a detecting element section having two elements disposed in opposition to each other and mounted in a diffusion chamber in which exhaust gas flows, each of the elements being made of an oxygen-ion-conductive solid electrolyte provided with porous electrodes on its opposite surfaces. A theoretical air-fuel ratio detecting device is provided for detecting the theoretical air-fuel ratio to produce a theoretical air-fuel signal for determining whether the air-fuel ratio is in the lean region or in the rich region, in which one of the two elements is employed as an oxygen sensing element and the other as an oxygen pumping element, whereby the electromotive force of the oxygen sensing element or the pumping current flowing in the oxygen pumping element is controlled so as to obtain an air-fuel ratio signal accurately corresponding to the air-fuel ratio in each of the lean and rich regions. The thus-obtained air-fuel ratio signal is inverted on the basis of the theoretical air-fuel ratio signal produced by the theoretical air-fuel ratio detecting device when the air-fuel ratio is in the rich or lean region, thereby making it possible to produce an air-fuel ratio signal accurately corresponding to the actual air-fuel ratio over the entire operating range, that is, in both rich and lean regions.

Therefore, by employing the air-fuel ratio detecting device according to the present invention, the air-fuel ratio of an air-fuel mixture supplied to a combustion device such as an engine or the like can be accurately detected, and the air-fuel ratio can be feedback controlled to maintain a described air-fuel ratio, thereby making it possible to realize more accurate air-fuel ratio control.

We claim:

1. An air-fuel ratio detecting device comprising:
   a detecting element section having two elements arranged in opposition to one another and disposed in a chamber in which an exhaust gas flows, each of said elements being made of an oxygen-ion-conductive solid electrolyte provided with porous electrodes on its opposite surfaces;
   theoretical air-fuel ratio detecting means for detecting a theoretical air-fuel ratio to produce a theoretical air-fuel ratio signal indicative of whether an air-fuel ratio is in a lean region or in a rich region;
   air-fuel ratio signal detecting means, employing one of said two elements in said detecting element section as an oxygen sensing element and the other as an oxygen pumping element, for controlling one of an electromotive force of said oxygen sensing element and a pumping current flowing in said oxygen pumping element, wherein an air-fuel ratio signal corresponding to the air-fuel ratio in each of lean and rich regions of said air-fuel ratio is produced; and
   actual air-fuel ratio signal detecting means receiving said theoretical air-fuel ratio signal produced by said theoretical air-fuel ratio detecting means and said air-fuel ratio signal produced by said air-fuel ratio signal detecting for deriving an actual air-fuel ratio signal corresponding to an actual air-fuel ratio over an entire range of air-fuel ratios in accordance with said theoretical air-fuel ratio signal and said air-fuel ratio signal, wherein a polarity of said air-fuel ratio signal produced by said air-fuel ratio signal detecting means is inverted in accordance with a value of said theoretical air-fuel ratio signal.

2. The air-fuel ratio detecting device according to claim 1, wherein said actual air-fuel ratio signal detecting means comprises means for producing an actual air-fuel ratio signal which changes stepwise at a theoretical air-fuel ratio.

3. The air-fuel ratio detecting device according to claim 1, wherein said theoretical air-fuel ratio detecting means comprises a theoretical air-fuel ratio detecting element made of an electrically insulating member provided with a metal oxide semiconductor segment on a surface thereof.

4. The air-fuel ratio detecting device according to any one of claims 1 to 3, wherein said air-fuel ratio signal detecting means comprises means for controlling said pumping current of said oxygen pumping element so as to make an electromotive force of said oxygen sensing element constant, said pumping current forming said air-fuel ratio signal.

5. The air-fuel ratio detecting device according to any one of claims 1 to 3, wherein a gap is formed between said two elements, said gap being opened at an edge portion thereof.

* * * * *